United States Patent [19]

Hendi

[11] Patent Number: 5,786,487

[45] Date of Patent: Jul. 28, 1998

[54] 1,4-DIKETO-3,6-DIARYLPYROLO[3,4-C] PYRROLE PIGMENT DERIVATIVES

[75] Inventor: Shivakumar B. Hendi, Newark, Del.

[73] Assignee: Ciba Specialty Chemicals Corporation, Tarrytown, N.Y.

[21] Appl. No.: 938,658

[22] Filed: Sep. 26, 1997

Related U.S. Application Data

[60] Provisional application No. 60/027,469 Sep. 26, 1996 and provisional application No. 60/041,521 Mar. 24, 1997.

[51] Int. Cl.$^6$ .................................................. C07D 487/04
[52] U.S. Cl. .......................... 548/453; 106/498; 544/144; 544/333; 544/373; 546/199; 546/277.1; 548/159; 548/217; 548/235; 548/255; 548/266.4; 548/305.1; 548/311.7; 548/364.7
[58] Field of Search ............................. 548/453; 106/498

[56] References Cited

U.S. PATENT DOCUMENTS 4,585,878 4/1986 Jost et al. ........................... 548/453
5,527,922 6/1996 Zambounis et al. ............... 548/453

*Primary Examiner*—Fiona T. Powers
*Assistant Examiner*—Laura L. Stockton
*Attorney, Agent, or Firm*—George R. Dohmann; Kevin T. Mansfield

[57] ABSTRACT

The present invention relates to pyrrolopyrrole derivatives of the formula (I)

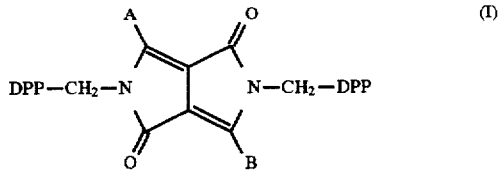

wherein A and B are identical or different aryl radicals, and DPP is a diaryldiketopyrrolopyrrole radical; which diketopyrrolopyrrole derivative is substituted by from 0 to 6 moles of —$SO_3M$ per mole of the pyrrolopyrrole derivative; wherein M is hydrogen or a metal or ammonium cation. The pyrrolopyrrole derivatives of formula I are useful as rheology-improving agents for pigment dispersions.

31 Claims, No Drawings

1,4-DIKETO-3,6-DIARYLPYROLO[3,4-C] PYRROLE PIGMENT DERIVATIVES

This application claims the benefit under 35 U.S.C. 119(e) of U.S. Provisional Application No.'s 60/027,469, filed Sep. 26, 1996 and 60/041,521, filed Mar. 24, 1997.

SUMMARY

The present invention relates to derivatives of 1,4-diketo-3,6-diarylpyrrolo[3,4-c]pyrrole pigments, pigment compositions containing the new derivatives and to the use of the new derivatives to improve the rheology of a pigment dispersion in a high-molecular-weight organic material and/or the coloristic characteristics of an automotive finish.

BACKGROUND 3,6-Diaryl-1,4-diketopyrrolopyrrole (DPP) compounds are well-known as important organic pigments. Generally, these pigments are described by the formula

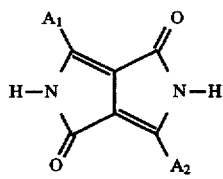

wherein $A_1$ and $A_2$ are aryl radicals.

U.S. Pat. No. 4,585,878 discloses N-substituted derivatives of the diaryldiketopyrrolopyrrole pigments wherein the N-substituent does not confer solubility in water. According to U.S. Pat. No. 4,585,878 the disclosed derivatives are useful as polymer soluble dyes or as pigments.

Rheology-improving agents for organic pigments reduce the viscosity of a dispersion of the organic pigment in a high-molecular-weight organic material. Some compounds capable of functioning as rheology-improving agents for organic pigments are known. For example, phthalimidomethylquinacridone, quinacridone monosulfonic acid salts, especially the aluminum salt, the dimethylaminopropylsulfonamide derivative of quinacridone and pyrrazolylmethylquinacridone are known rheology improving agents for organic pigments.

Although the known rheology improving agents adequately reduce the viscosity when the organic pigment is dispersed in a high molecular weight organic material, the incorporation of the known rheology improving agents in a pigment composition based on a bright red or highly saturated orange pigment generally results in unacceptable pigmentary properties with significant loss in color and color saturation.

The present invention relates to a new class of rheology-improving agent for organic pigments; the pyrrolopyrrole derivatives of the formula (I)

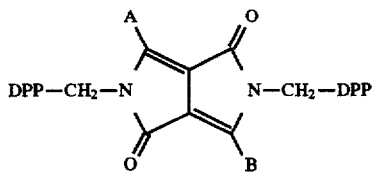

wherein DPP is a diaryldiketopyrrolopyrrole radical. As rheology-improving additives for organic pigments, especially quinacridones, DPPs and their solid solution pigments, the inventive pyrrolopyrrole derivatives provide excellent rheology-enhancing properties, but do not adversely impact on the coloristic and/or hiding properties of the pigment composition to which they are added.

DETAILED DESCRIPTION

The present invention relates to pyrrolopyrrole derivatives of the formula (I)

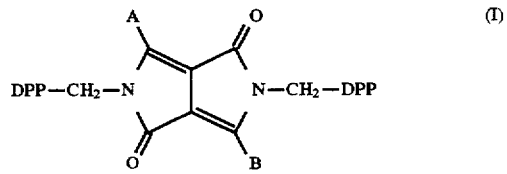

wherein A and B are identical or different aryl radicals, and DPP is a diaryldiketopyrrolopyrrole radical; which diketopyrrolopyrrole derivative is substituted by from 0 to 6 moles of —$SO_3M$ per mole of the pyrrolopyrrole derivative; wherein M is hydrogen or a metal or ammonium cation. When M is a metal cation it is preferably a cation of sodium, potassium or lithium.

Preferably, the pyrrolopyrrole derivative is substituted with from 0 to 2 moles of —$SO_3M$ per mole of DPP derivative, most preferably 0 to 0.75 moles of —$SO_3M$ per mole of DPP derivative. Important pyrrolopyrrole derivatives contain virtually no —$SO_3M$.

Preferably, DPP is a diaryldiketopyrrolopyrrole radical of the formula

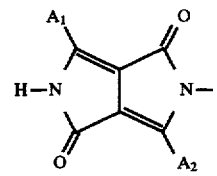

wherein $A_1$ and $A_2$ are aryl radicals.

A, B, $A_1$ and $A_2$ as aryl radicals include both aromatic and heteroaromatic radicals.

Radicals which are particularly suitable as A, B, $A_1$ and $A_2$ include radicals of the formula

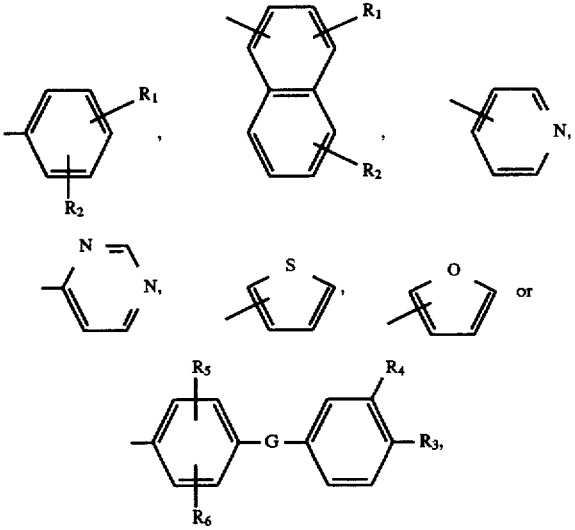

wherein $R_1$ and $R_2$ are each independently of the other hydrogen, halogen, $C_1$-$C_{18}$alkyl, $C_1$-$C_{18}$alkoxy, $C_1$–$C_{18}$alkylmercapto, $C_1$–$C_{18}$alkylamino, $C_1$–$C_{18}$alkoxycarbonyl, $C_1$–$C_{18}$alkylaminocarbonyl, —CN, —NO$_2$, trifluoromethyl, $C_5$–$C_6$cycloalkyl, —C=N—($C_1$–$C_{18}$alkyl), phenyl,

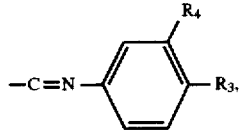

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$—, —CONH— or —NR$_7$—, R$_3$ and R$_4$ are each independently of the other hydrogen, halogen, $C_1$–$C_6$alkyl, $C_1$–$C_{18}$alkoxy or —CN, R$_5$ and R$_6$ are each independently of the other hydrogen, halogen or $C_1$–$C_6$alkyl, and R$_7$ is hydrogen or $C_1$–$C_6$alkyl.

In particular, A, B, A$_1$ and A$_2$ are each a group of formula

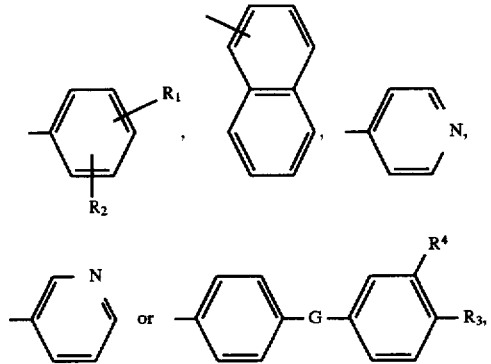

wherein

R$_1$ and R$_2$ are each independently of the other hydrogen, chloro, bromo, $C_1$–$C_4$alkyl, $C_1$–$C_6$alkoxy, $C_1$–$C_6$alkylamino, phenyl or CN, G is —O—, —NR$_7$—, —N=N— or —SO$_2$—, R$_3$ and R$_4$ are hydrogen, and R$_7$ is hydrogen, methyl or ethyl, and more particularly A, B, A$_1$ and A$_2$ are each a group of formula

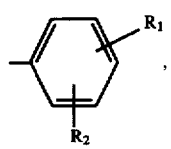

wherein R$_1$ and R$_2$ are each independently of the other hydrogen, methyl, tert-butyl, chloro, bromo, phenyl or CN. At least one of R$_1$ and R$_2$ is preferably hydrogen. Most preferably, at least one of R$_1$ and R$_2$ is hydrogen and the other is in the 3- or 4-position of the phenyl ring.

Especially important compounds are those wherein A and B are identical and are selected from the group consisting of phenyl, 4-methylphenyl, 4-tert-butylphenyl, 4-chlorophenyl, 4-bromophenyl and biphenyl-1-yl (4-phenyl-phenyl); especially those wherein A$_1$ and A$_2$ are also identical and selected from the group consisting of phenyl, 4-methylphenyl, 4-tert-butylphenyl, 4-chlorophenyl, 4-bromophenyl and biphenyl-1-yl.

An important class of pyrrolopyrrole derivatives are those wherein A$_1$ and A$_2$ are each 4-tertbutylphenyl; especially those wherein A and B are identical and selected from phenyl, 4-tertbutylphenyl and 4-methylphenyl; especially 4-tertbutylphenyl. Such pyrrolopyrrole derivatives provide excellent rheology improvement properties when incorporated into a pigment composition, but additionally provide enhancement of desirable pigment properties such as hiding (opacity) and color saturation. Thus, the pyrrolopyrrole derivative wherein A, B, A$_1$ and A$_2$ are each 4-tertbutylphenyl represents an especially important compound of the present invention.

Another important class of pyrrolopyrrole derivatives are those wherein A$_1$ and A$_2$ are each 4-methylphenyl; and A and B are identical and selected from the group consisting of phenyl, 4-tertbutylphenyl and 4-methylphenyl; especially 4-tertbutylphenyl.

The pyrrolopyrrole derivatives of the present invention are especially suitable for use as rheology-improving agents for organic pigments. As rheology-improvings agents for organic pigments, the inventive pyrrolopyrrole derivatives function to reduce the viscosity of a dispersion of the pigment composition in a high-molecular-weight organic material, such as a coating composition, for example, a water-borne or solvent-borne automotive paint.

Thus, another aspect of this invention relates to pigment compositions which comprise an organic pigment and a pyrrolopyrrole derivative of formula (I). Preferably, the pigment composition contains from 0.1 to 20 percent by weight of the pyrrolopyrrole derivative. Most preferably, the pigment composition contains from 1 to 10 percent by weight of the pyrrolopyrrole derivative.

Preferably, the pyrrolopyrrole derivative of formula (I) is selected such that A, B, A$_1$ and A$_2$ are each a group of formula

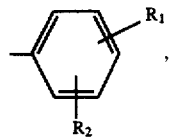

wherein R$_1$ and R$_2$ are each independently of the other hydrogen, methyl, tert-butyl, chloro, bromo, phenyl or CN. At least one of R$_1$ and R$_2$ is preferably hydrogen. Most preferably, at least one of R$_1$ and R$_2$ is hydrogen and the other is in the 3- or 4-position of the phenyl ring.

Important pigment compositions according to the present invention are those which contain a 1,4-diketo-3,6-diarylpyrrolo[3,4-c]pyrrole pigment or a quinacridone pigment as the organic pigment and a pyrrolopyrrole derivative of the formula (I); including their solid solutions.

The inventive pigment compositions especially include those containing a 1,4-diketo-3,6-diarylpyrrolo[3,4-c]pyrrole pigment selected from the group consisting of unsubstituted 1,4-diketo-3,6-diphenylpyrrolo[3,4-c]pyrrole, 1,4-diketo-3,6-di(3- or 4-chlorophenyl)pyrrolo[3,4-c]pyrrole, 1,4-diketo-3,6-di(3,4-dichlorophenyl)pyrrolo[3,4-c]pyrrole, 1,4-diketo-3,6-di(3-cyanophenyl)pyrrolo[3,4-c]pyrrole, 1,4-diketo-3,6-di(4-tert-butylphenyl)pyrrolo[3,4-c]pyrrole, 1,4-diketo-3,6-di(4-methylphenyl)pyrrolo[3,4-c]pyrrole, and 1,4-diketo-3,6-di(biphenyl-1-yl)pyrrolo[3,4-c]pyrrole, and a pyrrolopyrrole derivative of formula (I).

In addition, the inventive pigment compositions especially include those containing a quinacridone pigment selected from the group consisting of unsubstituted quinacridone, 2,9- and 4,11-dimethylquinacridone, 2,9- and 4,11-dichloroquinacridone and 2,9- and 4,11-difluoroquinacridone and a pyrrolopyrrole derivative of formula (I).

Especially important pigment compositions are those containing a 1,4-diketo-3,6-diarylpyrrolo[3,4-c]pyrrole pigment selected from the group consisting of unsubstituted 1,4-diketo-3,6-diphenylpyrrolo[3,4-c]pyrrole and 1,4-diketo-3,6-di(4-tert-butylphenyl)pyrrolo[3,4-c]pyrrole in combination with a pyrrolopyrrole derivative of formula (I) wherein $A_1$ and $A_2$ are each 4-tertbutylphenyl; especially those wherein A and B are identical and selected from phenyl, 4-tertbutylphenyl and 4-methylphenyl; especially 4-tertbutylphenyl.

Although the pigment compositions of the present invention can consist of only the organic pigment and the pyrrolopyrrole derivative, the pigment compositions generally contain customary additives, such as texture improving agents, light stabilizers and especially a second rheology-improving agent.

Useful light stabilizers are U.V. light absorbers, for example, benzotriazoles or hindered amine light stabilizers (HALS).

Texture-improving agents are especially useful as an additional component which can improve the properties of the stir-in pigment compositions. Suitable texture-improving agents include fatty acids having at least 12 carbon atoms, and amides, esters or salts of fatty acids. Typical fatty acid derived texture-improving agents include fatty acids such as stearic acid or behenic acid, and fatty amines such as lauryl amine, or stearylamine. In addition, polyols, such as aliphatic 1,2-diols or polyvinyl alcohol, and ethoxylated fatty alcohols, epoxidized soya bean oil, waxes, resin acids and resin acid salts are suitable texture-improving agents. Rosin acids and rosin acid salts are especially suitable texture-improving agents. In general, the inventive pigment compositions contain from 0 to 20 percent by weight of the texture improving agent, preferably 0.5 to 10 percent by weight.

Agents useful as the second rheology-improving agent in the present pigment compositions include quinacridone derivatives, such as, quinacridone sulfonic acid, or a salt thereof, especially the aluminum salt, or pyrazolylmethylquinacridone, or other pyrrolopyrrole (DPP) derivatives, such as, a DPP sulfonic acid, or salt thereof, or a DPP derivative of the formula QA—CH$_2$—DPP—CH$_2$—QA, wherein QA is a radical derived from a quinacridone pigment which is prepared by methods analogous to those used to prepare the DPP—CH$_2$—DPP—CH$_2$—DPP derivatives which are the subject of the present application. If the pigment composition includes a second rheology-improving agent, the combined parts by weight of the pyrrolopyrrole derivative of formula (I) and the second rheology-improving agent are preferably in the range from 0.2 to 20 parts by weight per part of the pigment; most preferably from 2 to 10 parts per part of the pigment.

As discussed above, the presence of an inventive pyrrolopyrrole derivative in a dispersion of an organic pigment in a high-molecular-weight organic material effectively reduces the viscosity of the dispersion. Thus, the present invention further relates to a method of reducing the viscosity of a dispersion of an organic pigment in a high molecular weight organic material which comprises incorporating an effective viscosity-reducing amount of a pyrrolopyrrole derivative of formula (I) into the dispersion.

The pyrrolopyrrole derivative of formula (I) is added to the dispersion on its own, or, preferably, as a component of a pigment composition.

Preferably, the pyrrolopyrrole derivative of formula (I) is chosen such that A, B, $A_1$ and $A_2$ are each a group of formula

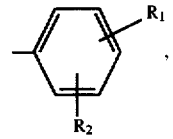

wherein $R_1$ and $R_2$ are each independently of the other hydrogen, methyl, tert-butyl, chloro, bromo, phenyl or CN. At least one of $R_1$ and $R_2$ is preferably hydrogen. Most preferably, at least one of $R_1$ and $R_2$ is hydrogen and the other is in the 3- or 4-position of the phenyl ring.

Preferably, the pyrrolopyrrole derivative of formula (I) is present in the dispersion in an amount in the range from 0.1 to 20 parts by weight per part of the pigment dispersion. More preferably, the pyrrolpyrrole derivative of formula (I) is present in the dispersion in an amount in the range from 0.2 to 10 parts by weight per part of the pigment dispersion. If the pyrrolopyrrole derivative of formula (I) is combined with a second rheology-improving agent, the combined parts by weight of the pyrrolopyrrole derivative of formula (I) and the second rheology-improving agent are preferably in the range from 0.1 to 20 parts by weight per part of the pigment dispersion; most preferably from 0.2 to 10 parts per part of the pigment dispersion.

The organic pigment is an azo, azomethine, anthraquinone, phthalocyanine, perinone, perylene, 1,4-diketo-3,6-diarylpyrrolo[3,4-c]pyrrole, thioindigo, isoindoline, isoindolinone, quinacridone, flavanthrone, indanthrone, anthrapyrimidine or quinophthalone pigment; in particular a 1,4-diketo-3,6-diarylpyrrolo[3,4-c]pyrrole or quinacridone pigment.

The high-molecular-weight organic materials are, for example, cellulose ethers, cellulose esters, polyurethanes, polyesters, polycarbonates, polyolefins, polystyrene, polysulfones, polyamides, polycycloamides, polyimides, polyethers, polyether ketones, polyvinyl halides, polytetrafluoroethylene, acrylic and methacrylic polymers, rubber, silicone polymers, phenol/formaldehyde resins, melamine, formaldehyde resins, urea/formaldehyde resins, epoxy resins and diene rubbers or copolymers thereof.

The dispersions especially contain a high molecular weight organic material which is useful for heat-curable or cross-linked coatings, for example chemically-reactive coatings, including stoving finishes which contain the customary binders and which are reactive at high temperature. Examples of the high molecular weight organic materials which are used in such coatings include acrylic, alkyd, epoxy, phenolic, melamine, urea, polyester, polyurethane, blocked isocyanate, benzoguanamine or cellulose ester resins, or combinations thereof. The pigmented, high molecular weight organic materials prepared according to the present process are also useful as air-drying or physically-drying coatings, for example, conventional lacquers such as those used in the cosmetics industry as nail varnishes, for example nitrocellulose lacquers.

The present process is particularly suitable for reducing the viscosity of dispersions containing high molecular weight organic materials conventionally employed as finishes in the automobile industry, especially acrylic/melamine resin, alkyd/melamine resin or thermoplastic acrylic resin systems, as well as in aqueous-based coating systems.

The use of many of the known viscosity-reducing agents for pigment dispersions often results in at least some loss of saturation when the pigment dispersion is applied as the basecoat in a basecoat/clearcoat automotive finish. However, the use of the present pyrrolopyrrole derivatives of formula (I) as viscosity-reducing agents surprisingly does not result in loss of saturation when the pigment dispersion is applied as the basecoat in a basecoat/clearcoat automotive finish, indeed in many instances the saturation of the finish is increased by the presence of the pyrrolopyrrole derivative of formula (I). Thus, the present invention further relates to a method of preparing a basecoat/clearcoat finish, which comprises the step of applying a dispersion comprising an effective viscosity-reducing and saturation-enhancing amount of a pyrrolopyrrole derivative of formula (I) in a high molecular weight organic compound to a substrate; especially wherein, in the compounds of formula (I), $A_1$ and $A_2$ are each 4-tert-butylphenyl; and A and B are identical and selected from the group consisting of phenyl, 4-tertbutylphenyl and 4methylphenyl; especially 4-tert-butylphenyl.

A preferred embodiment of the present invention relates to coating composition, such as an automotive finish, which comprises a high molecular weight organic material, a red- or orange-colored organic pigment and a pyrrolopyrrole derivative of the formula (I) wherein $A_1$ and $A_2$ are each 4-tertbutylphenyl; especially those wherein A and B are identical and selected from phenyl, 4-tertbutylphenyl and 4-methylphenyl; especially phenyl. Thus, a preferred embodiment of this invention includes a coating composition, which comprises a high-molecular-weight organic material, a red- or orange-colored organic pigment and a pyrrolopyrrole derivative of the formula (I) wherein A, B, $A_1$ and $A_2$ are each phenyl.

Preferably, the red- or orange-colored organic pigment is selected from the group consisting of unsubstituted 1,4-diketo-3,6-diphenylpyrrolo[3,4-c]pyrrole and 1,4-diketo-3,6-di(4-tert-butylphenyl)pyrrolo[3,4-c]pyrrole.

Preferably, the high-molecular-weight organic material is an acrylic/melamine resin, alkyd/melamine resin or thermoplastic acrylic resin.

Preferences discussed above for the pyrrolopyrrole derivatives relate to all other aspects of this invention.

In this application, the expression "automotive finish" is used to describe finishes typically used for automobiles, such as waterborne and solventborne basecoat/clearcoat finishes. Such finishes are used for numerous applications other than for automobiles, such as other motor vehicles, bicycles, and appliances.

The present pyrrolopyrrole derivatives are easily prepared by a process which comprises a reaction wherein a first 1,4-diketo-3,6-diarylpyrrolo[3,4-c]pyrrole of the formula

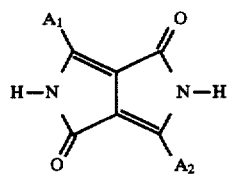

is reacted in a first step with formaldehyde to yield a sulfonated or non-sulfonated intermediate of the formula

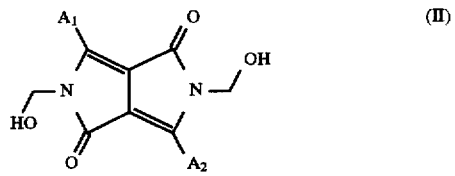

which intermediate reacts in a second step with 2 moles of a second 1,4-diketo-3,6-diarylpyrrolo[3,4-c]pyrrole to yield the pyrrolopyrrole derivative of formula (I).

The first step is preferably carried out by adding the first 1,4-diketo-3,6-diarylpyrrolo[3,4-c]pyrrole to a solution of paraformaldehyde in concentrated sulfuric acid, preferably having a $H_2SO_4$ concentration greater than 90 percent by weight, most preferably above 95 percent by weight.

In general, the stoichiometric amount of formaldehyde is used in the first step. Thus, the molar ratio of the first 1,4-diketo-3,6-diarylpyrrolo[3,4-c]pyrrole to the formaldehyde during the first step is preferably 1:2.

After step (a) is complete, the resulting intermediate is reacted with two moles of the second 1,4-diketo-3,6-diarylpyrrolo[3,4-c]pyrrole to yield the pyrrolopyrrole derivative of formula (I).

Preferably, both steps are carried out at a temperature of from 20° to 100° C. If a high degree of sulfonation is desired, the process is carried out at higher temperatures, for example above 40° C. If it is desirable to have a low degree of sulfonation, the reaction is maintained at a lower temperature, preferably 40° C. or below.

After the reaction is complete, the pyrrolo[3,4-c]pyrrole derivative of formula (I) is isolated by procedures conventionally used in the art for isolating 1,4-diketo-3,6-diarylpyrrolo[3,4-c]pyrroles, in particular by pouring the sulfuric acid solution into ice water maintaining the temperature below 10° C. and stirring the resulting aqueous slurry for about 1 hour, followed by filtration, washing and drying to yield the 1,4-diketo-3,6-diarylpyrrolo[3,4-c]pyrrole derivative in solid form.

The following examples further describe the embodiments of the invention, but do not limit the scope of the invention. In the examples, all parts are by weight unless otherwise indicated. All viscosity measurements are taken at room temperature.

EXAMPLE 1

250 grams of concentrated sulfuric acid (96%) and paraformaldehyde (3.3 g.; 0.11 moles) are added to a one liter four necked flask, equipped with a stirrer, a thermometer, a reflux condenser with a drying tube. Unsubstituted DPP(14.4 g.; 0.05 moles) are added to the sulfuric acid/paraformaldehyde mixture in small portions maintaining the pot temperature between 25°–30° C. This mixture is stirred for 1 hour to ensure complete solution. An additional 200 g of sulfuric acid is then added to the reaction mixture followed by unsubstituted DPP(28.8 g.; 0.1 moles) in small portions, maintaining the pot temperature at 32°–34° C. This reaction mixture is then stirred at 30°±3° C. for 4 hrs and poured into ice-water, filtered, washed with water until the filtrate is acid free, dried and pulverized.

The compound isolated analyzed for $C_{56}H_{36}N_6O_6$ and is believed to have the formula (III)

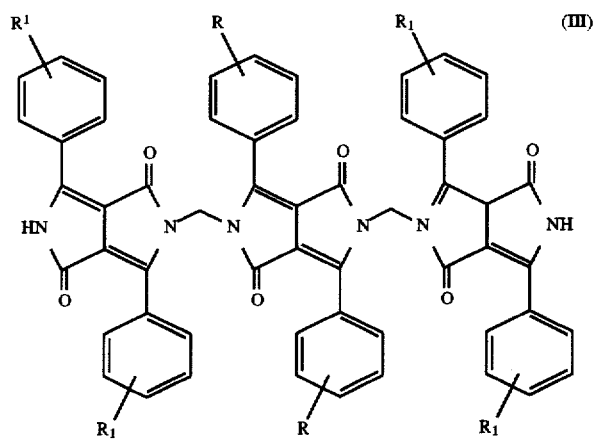

(III)

wherein each R and R₁ substituent is hydrogen.

The compounds in Table 1 are made by substituting the appropriate pyrrolopyrrole reactants in the process of Example 1.

TABLE 1

DPP-CH₂-DPP-CH₂-DPP derivatives

| R | R₁ | crystallize from |
|---|-----|------------------|
| H | H | $H_2SO_4$ |
| H | Cl | $H_2SO_4$ |
| H | CH₃ | $H_2SO_4$ |
| H | t-Butyl | $H_2SO_4$ |
| H | 4-Phenyl | $H_2SO_4$ |
| Cl | H | $H_2SO_4$ |
| Cl | Cl | $H_2SO_4$ |
| Cl | CH₃ | $H_2SO_4$ |
| Cl | t-Butyl | $H_2SO_4$ |
| Cl | 4-Phenyl | $H_2SO_4$ |
| CH3 | H | $H_2SO_4$ |
| CH3 | Cl | $H_2SO_4$ |
| CH3 | CH₃ | $H_2SO_4$ |
| CH3 | t-Butyl | $H_2SO_4$ |
| CH3 | 4-Phenyl | $H_2SO_4$ |
| t-Butyl | H | $H_2SO_4$ |
| t-Butyl | Cl | $H_2SO_4$ |
| t-Butyl | CH₃ | $H_2SO_4$ |
| t-Butyl | t-Butyl | $H_2SO_4$ |
| t-Butyl | 4-Phenyl | $H_2SO_4$ |
| 4-Phenyl | H | $H_2SO_4$ |
| 4-Phenyl | Cl | $H_2SO_4$ |
| 4-Phenyl | CH₃ | $H_2SO_4$ |
| 4-Phenyl | t-Butyl | $H_2SO_4$ |
| 4-Phenyl | 4-Phenyl | $H_2SO_4$ |

EXAMPLE 2

250 grams of concentrated sulfuric acid (96%) and paraformaldehyde (3.3 g; 0.11 moles) are added to a one liter four necked flask equipped with a stirrer, a thermometer, a reflux condenser with a drying tube. Unsubstituted DPP (14.4 g; 0.05 moles) are added to the sulfuric acid/ paraformaldehyde mixture in small portions maintaining the pot temperature between 30°–35° C. This mixture is stirred for 1 hour to ensure complete solution. An additional 200 g of sulfuric acid is then added to the reaction mixture followed by unsubstituted DPP(28.8 g; 0.1 moles) in small portions, maintaining the pot temperature at 38°–42° C. This reaction mixture is then stirred at 40°±3° C. for 4 hrs and poured into ice-water, filtered, washed with water until the filtrate is acid free, dried and pulverized.

The compound isolated analyzed for $C_{56}H_{36}N_6O_6 \cdot (SO_3H)_{0.5}$

The sulfonated derivatives of the compounds of Table 1 are prepared by substituting the appropriate pyrrolopyrrole reactants in the process of Example 2.

EXAMPLE 3

An organic ternary solid solution pigment which is composed of dichloro DPP/unsubstituted DPP/2,9-dichloroquinacridone (48%/32%/20%), is combined with a rheology-improving agent composed of 4% quinacridone monosulfonic acid, aluminum salt (QMA) and 4% of the pyrrolopyrrole derivative of Example 1 by adding the rheology-improving agent to an aqueous suspension of the pigment, filtering and washing to yield the pigment composition. Rheology profiles of pigment dispersions in a commercial high solids solventborne paint formulation containing about 12% by weight of the pigment at a pigment to binder ratio of 0.5% are depicted in the Table 2.

TABLE 2

MILLBASE VISCOSITY (BROOKFIELD)

Paint System: BC/CC; % Pigment: 12.0%; P/B = 0.5

| Sample ID | Rheology-improving Agent | 50 RPM |
|-----------|--------------------------|--------|
| 3a | Untreated | 3660 |
| 3b | 4% QMA + 4% Example 1 R=R₁=H | 828 |

EXAMPLE 4

An orange-colored di(t-butylphenyl)-DPP pigment is combined with a rheology-improving agent described according to formula (III). Rheology profiles of pigment dispersions in a commercial high solids solventborne paint formulation containing about 16% by weight of the pigment at a pigment to binder ratio of 0.5% measured after 4 hours of attritor milling are depicted in the Table 3.

TABLE 3

Millbase Viscosity (Brookfield)

| sample | Rheology-improving Agent | 50 rpm |
|--------|--------------------------|--------|
| 4a | 4% R=H; R₁=CH₃ | 868 |
| 4b | 8% R=H; R₁=CH₃ | 546 |
| 4c | 4% R=R₁=t-Bu | 670 |
| 4d | 8% R=R₁=t-Bu | 528 |

The rheology-improving of examples 4c and 4d, in addition to the rheology improvements, improves the color saturation of the pigment when sprayed on a panel as part of a conventional basecoat/clearcoat automotive finish. Similarly improved color saturation is observed when a different red or orange pigment, for example quinacridone, is used in place of di(t-butylphenyl)-DPP.

EXAMPLE 5

An orange-colored di(t-butylphenyl)-DPP pigment is combined with the mixture of rheology-improving agents described in the Table 4 with R and R₁ being described according to formula (III) and PYMQ being pyrrazolylmethylquinacridone. Rheology profiles of pigment dispersions in a commercial high solids solventborne paint formulation containing about 16% by weight of the pigment at a pigment to binder ratio of 0.5% measured after 4 hours of attritor milling are depicted in the Table 4.

TABLE 4

| | Millbase Viscosity (Brookfield) | |
|---|---|---|
| Sample | Rheology-improving Agent | 50 rpm |
| 5 | no treatment | >2000 |
| 5a | 4% PYMQ | 954 |
| 5b | + 4% R=H; $R_1$=CH$_3$ 4% R=H; $R_1$=t-Bu | 1080 |
| 5c | + 4% R=H; $R_1$=CH$_3$ 2% R=H; $R_1$=t-Bu + 2% R=H; $R_1$=CH$_3$ | 1320 |

I claim:

1. A pyrrolopyrrole derivative of the formula (I)

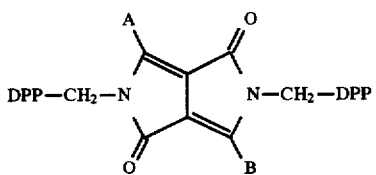
(I)

wherein A and B are identical or different aryl radicals, and DPP is a diaryldiketopyrrolopyrrole radical; which diketopyrrolopyrrole derivative is substituted by from 0 to 6 moles of —SO$_3$M per mole of the pyrrolopyrrole derivative; wherein M is hydrogen or a metal or ammonium cation.

2. A pyrrolopyrrole derivative of claim 1 having from 0 to 0.75 moles of —SO$_3$M per mole of DPP derivative.

3. A pyrrolopyrrole derivative of claim 1 wherein DPP is a diaryldiketopyrrolopyrrole radical of the formula

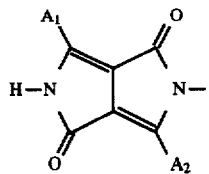

wherein $A_1$ and $A_2$ are aryl radicals.

4. A pyrrolopyrrole derivative of claim 3 wherein A, B, $A_1$ and $A_2$ are each independently a radical of the formula

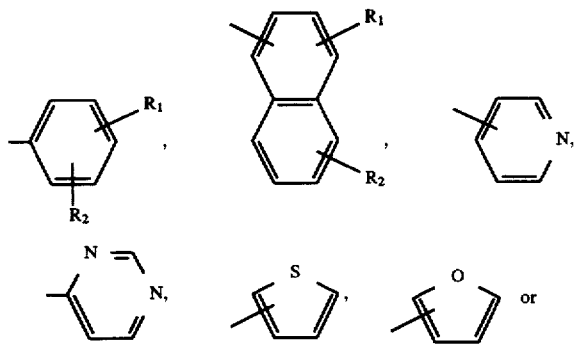

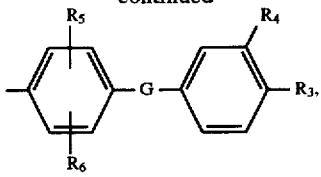

wherein
$R_1$ and $R_2$ are each independently of the other hydrogen, halogen, $C_1$-$C_{18}$alkyl, $C_1$-$C_{18}$alkoxy, $C_1$-$C_{18}$alkylmercapto, $C_1$-$C_{18}$alkylamino, $C_1$-$C_{18}$alkoxycarbonyl, $C_1$-$C_{18}$alkylaminocarbonyl, —CN, —NO$_2$, trifluoromethyl, $C_5$-$C_6$cycloalkyl, —C=N—($C_1$-$C_{18}$alkyl), phenyl,

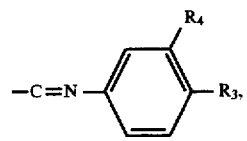

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, G is —CH$_2$—, —CH(CH$_3$)—, —C(CH$_3$)$_2$—, —CH=N—, —N=N—, —O—, —S—, —SO—, —SO$_2$—, —CONH— or —NR$_7$—, $R_3$ and $R_4$ are each independently of the other hydrogen, halogen, $C_1$-$C_6$alkyl, $C_1$-$C_{18}$alkoxy or —CN, $R_5$ and $R_6$ are each independently of the other hydrogen, halogen or $C_1$-$C_6$alkyl, and $R_7$ is hydrogen or $C_1$-$C_6$alkyl.

5. A pyrrolopyrrole derivative of claim 4, wherein A, B, $A_1$ and $A_2$ are each a group of formula

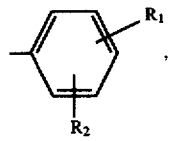

wherein $R_1$ and $R_2$ are each independently of the other hydrogen, methyl, tert-butyl, chloro, bromo, phenyl or CN.

6. A pyrrolopyrrole derivative of claim 5 wherein at least one of $R_1$ and $R_2$ is hydrogen.

7. A pyrrolopyrrole derivative of claim 4 wherein at least one of $R_1$ and $R_2$ is hydrogen and the other is in the 3- or 4-position of the phenyl ring.

8. A pyrrolopyrrole derivative of claim 1 wherein $A_1$ and $A_2$ are each 4-tert-butylphenyl; and A and B are identical and selected from the group consisting of phenyl, 4-tertbutylphenyl and 4-methylphenyl.

9. A pyrrolopyrrole derivative of claim 8 wherein A and B are 4-tert-butylphenyl.

10. A pyrrolopyrrole derivative of claim 1 wherein $A_1$ and $A_2$ are each 4-methylphenyl; and A and B are identical and selected from the group consisting of phenyl, 4-tertbutylphenyl and 4-methylphenyl.

11. A pyrrolopyrrole derivative of claim 10 wherein A and B are phenyl.

12. A pigment composition which comprises an organic pigment and a pyrrolopyrrole derivative of formula (I) according to claim 1.

13. A pigment composition of claim 12 which comprises from 1 to 10 percent by weight of the pyrrolopyrrole derivative of formula (I).

14. A pigment composition of claim 12, wherein A, B, A$_1$ and A$_2$ are each a group of formula

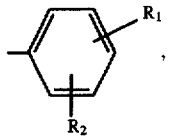

wherein R$_1$ and R$_2$ are each independently of the other hydrogen, methyl, tert-butyl, chloro, bromo, phenyl or CN.

15. A pigment composition of claim 14 wherein at least one of R$_1$ and R$_2$ is hydrogen.

16. A pigment composition of claim 14 wherein at least one of R$_1$ and R$_2$ is hydrogen and the other is in the 3- or 4-position of the phenyl ring.

17. A pigment composition of claim 12 wherein A$_1$ and A$_2$ are each 4-tert-butylphenyl; and A and B are identical and selected from the group consisting of phenyl, 4-tertbutylphenyl and 4-methylphenyl.

18. A pigment composition of claim 17 wherein A and B are 4-tert-butylphenyl.

19. A pigment composition of claim 12 wherein A$_1$ and A$_2$ are each 4-methylphenyl; and A and B are identical and selected from the group consisting of phenyl, 4-tertbutylphenyl and 4-methylphenyl.

20. A pigment composition of claim 19 wherein A and B are 4-tert-butylphenyl.

21. A pigment composition of claim 12 which further comprises a light stabilizer, a texture-improving agent or a second rheology-improving agent.

22. A pigment composition of claim 12 wherein the organic pigment is a 1,4-diketo-3,6-diarylpyrrolo[3,4-c] pyrrole pigment or a quinacridone pigment.

23. A pigment composition of claim 18 wherein the organic pigment is red or orange colored.

24. A method of reducing the viscosity of a dispersion of an organic pigment in a high molecular weight organic compound, which comprises incorporating an effective viscosity-reducing amount of a pyrrolopyrrole derivative of formula (I) according to claim 1 into the dispersion.

25. A method of claim 24 wherein the high molecular weight organic material is selected from cellulose ethers, cellulose esters, polyurethanes, polyesters, polycarbonates, polyolefins, polystyrene, polysulfones, polyamides, polycycloamides, polyimides, polyethers, polyether ketones, polyvinyl halides, polytetrafluoroethylene, acrylic and methacrylic polymers, rubber, silicone polymers, phenol/formaldehyde resins, melamine, formaldehyde resins, urea/formaldehyde resins, epoxy resins and diene rubbers or copolymers thereof.

26. A method of preparing a basecoat/clearcoat finish, which comprises the step of applying a dispersion comprising an effective viscosity-reducing and saturation-enhancing amount of a pyrrolopyrrole derivative of formula (I) according to claim 1 in a high-molecular-weight organic compound to a substrate.

27. A method of claim 26 wherein A$_1$ and A$_2$ are each 4-tert-butylphenyl; and A and B are identical and selected from the group consisting of phenyl, 4-tertbutylphenyl and 4-methylphenyl.

28. A method of claim 27 wherein A and B are 4-tert-butylphenyl.

29. A basecoat/clearcoat finish wherein the basecoat comprises a high molecular weight organic material, a red- or orange-colored organic pigment and a pyrrolopyrrole derivative of the formula (I) according to claim 1 wherein A$_1$ and A$_2$ are each 4-tert-butylphenyl; and A and B are identical and selected from phenyl, 4-tertbutylphenyl and 4-methylphenyl.

30. An basecoat/clearcoat finish of claim 29 wherein A and B are 4-tert-butylphenyl.

31. A coating composition, which comprises a high molecular weight organic material, a red- or orange-colored organic pigment and a pyrrolopyrrole derivative of the formula (I) according to claim 1 wherein A, B are phenyl and A$_1$ and A$_2$ are each 4-tert-butylphenyl.

* * * * *